United States Patent [19]
Wagner et al.

[11] 3,940,327
[45] Feb. 24, 1976

[54] OXYGEN SENSING DEVICE

[75] Inventors: Melvin H. Wagner; Sandra B. Corcoran, both of Bartlett; Carl F. Bauer, Chicago, all of Ill.

[73] Assignee: Universal Oil Products Company, Des Plaines, Ill.

[22] Filed: Apr. 11, 1975

[21] Appl. No.: 567,445

[52] U.S. Cl. .............................................. 204/195 S
[51] Int. Cl.² ......................................... G01N 27/46
[58] Field of Search ............ 204/195 S, 1 S; 324/29; 60/274, 276, 285, 289; 123/119 R, 119 E

[56] References Cited
UNITED STATES PATENTS

| 3,844,920 | 10/1974 | Burgett et al. ................... 204/195 S |
| 3,768,259 | 10/1973 | Carnahan et al. ............ 204/195 S X |
| 3,819,500 | 6/1974 | Van Esdonk et al. ............ 204/195 S |
| 3,847,778 | 11/1974 | Riddel ............................ 204/195 S |

Primary Examiner—G. L. Kaplan
Attorney, Agent, or Firm—James R. Hoatson, Jr.; Barry L. Clark; William H. Page, II

[57] ABSTRACT

Measuring cell for determining oxygen concentration in a combustion engine exhaust stream utilizes a wafer or disc of stabilized $ZrO_2$ as a solid electrolyte. A pair of concentric metal tubes having oppositely directed flanges contact electrode surfaces on the wafer and provide rugged electrical connections thereto. A pair of tubular ceramic sleeves positioned between the metal tubes electrically insulate the metal tubes from each other, seal (with the help of high temperature ceramic fiber gaskets) the wafer from leakage of exhaust gases to the reference side of the cell and space the wafer from the outer metal housing. The ceramic sleeves also maintain high temperature sealing and contact pressure between the tube flanges and the electrodes by virtue of the fact that they have a greater longitudinal length subject to temperature expansion than does the metal housing, thus making up for the fact that their temperature expansion coefficient per unit of length is lower.

10 Claims, 4 Drawing Figures

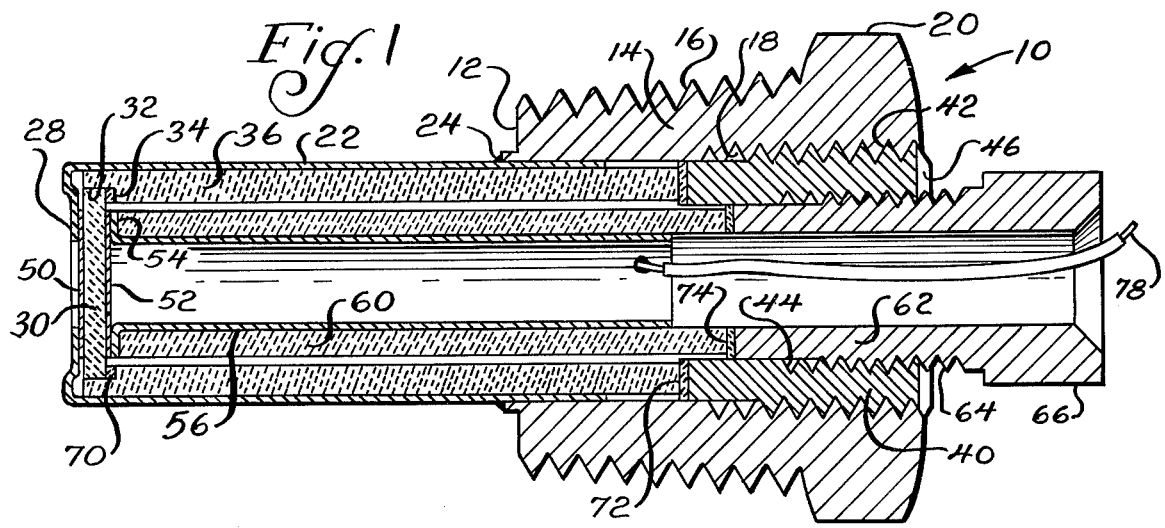
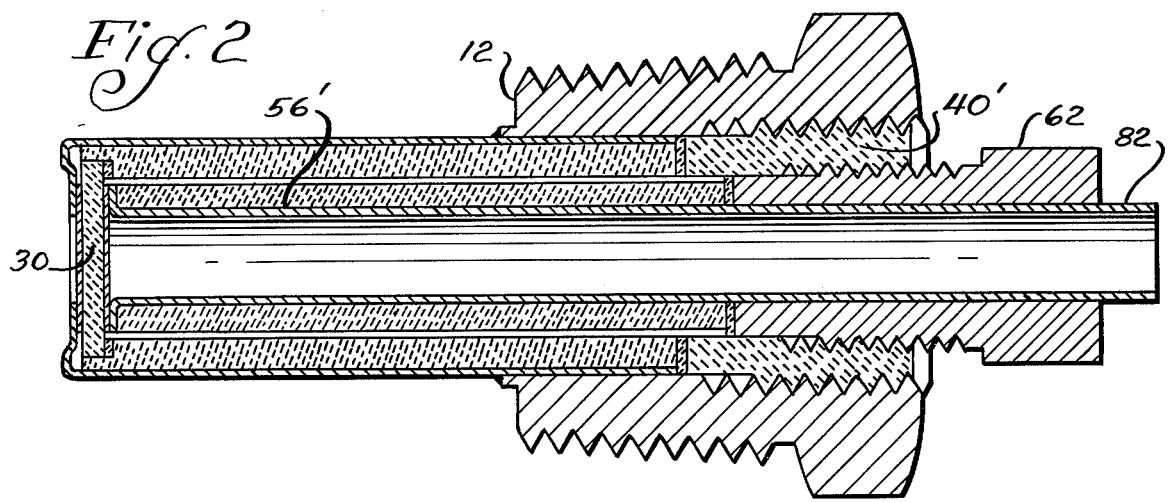
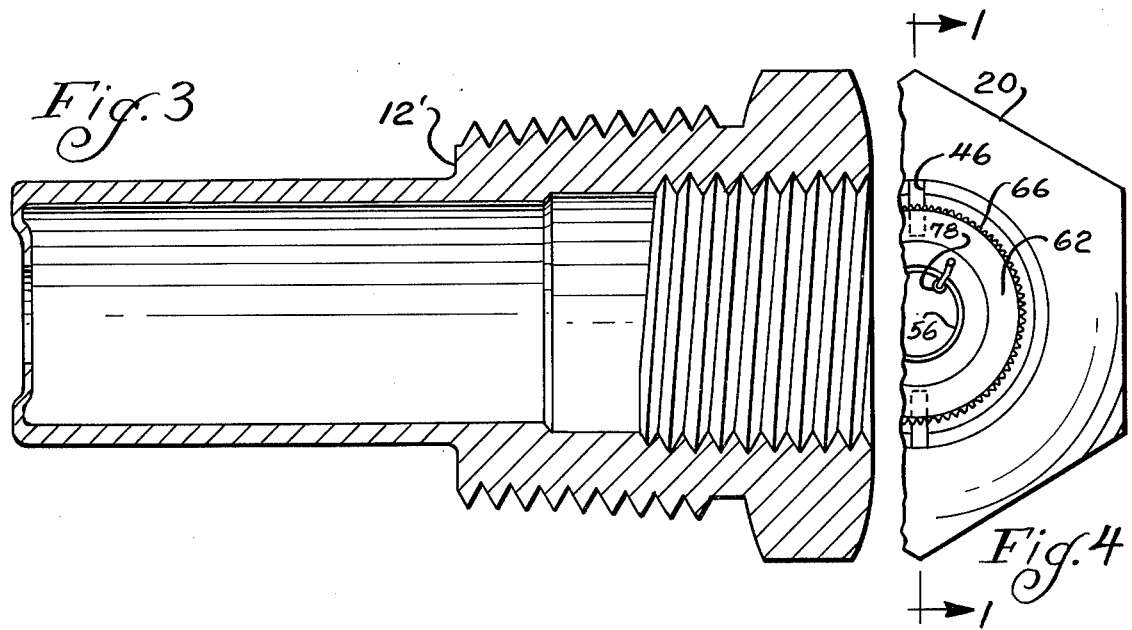

OXYGEN SENSING DEVICE

BACKGROUND OF THE INVENTION

The invention relates to solid electrolyte measuring cell devices of the type commonly referred to as oxygen sensors which are suitable for use in the exhaust path of an internal combustion engine. More particularly, the invention relates to a mounting and sealing arrangement for oxygen sensors of the so-called wafer or disc type wherein the solid electrolyte, which is preferably stabilized zirconium oxide, is in the form of a thin disc or wafer having a porous electrode coating on each side. A voltage is generated between the electrodes when there is a difference in oxygen partial pressures between the exhaust gas side of the electrolyte and the reference, or air side. Since the electrical signal is a maximum when the engine is operating stoichiometrically and combining all its CO with all of the excess oxygen, the sensor can be used as part of an air/fuel ratio control system to minimize pollutants. Examples of such wafer type sensors can be found in Carnahan et al U.S. Pat. No. 3,768,259 and in copending application Ser. No. 394,431, filed Sept. 4, 1973, each of which is assigned to a common assignee. Other wafer type sensors are disclosed in Van Esdonk et al Patent 3,819,500 and in East German Pat. No. 21,673 issued Apr. 7, 1961.

Despite the prior art attempts to achieve a durable oxygen sensor which will have a long life in the rugged environment of an automotive exhaust stream, problems such as seal leakage caused by the extreme temperature range experienced in the exhaust stream, electrical short circuits, lead breakage, and expensive construction techniques have combined to prevent the development of a durable and leak-tight sensor which can be produced in mass production at a relatively low cost. Auto manufacturers and others have developed electronic systems to process the information produced by an oxygen sensor as well as other systems to use the sensor information to control the operation of an engine to achieve maximum performance, fuel economy and freedom from exhaust pollutants. It would therefore seem to be most desirable to have an exhaust gas sensor which overcomes the durability and sealing problems of prior art structures and which can be made in mass production to high standards of uniformity.

SUMMARY

It is among the objects of the present invention to provide an exhaust gas or oxygen sensor which overcomes the aforesaid problems of the prior art. The improved sensor does not use springs to maintain electrical contacts and thus eliminates the inherent problem that a spring would rapidly fail in the high temperature environment of an exhaust system. It eliminates direct attachment of a lead member to the wafer and thus avoids the common problem of lead wire breakage and a very critical and complicated joining operation. Finally, the invention eliminates the problem of not being able to provide a mechanical hermetic seal between members having different coefficients of expansion and which are subjected to a very large temperature gradient.

The exhaust gas sensor of the present invention comprises a threaded outer metal bushing which has threads like a spark plug and which is adapted to be threaded into an opening in the side of the exhaust pipe of a combustion engine. The inner end of the sensor housing is generally tubular but has an inwardly flanged end which contacts an annular portion of an electrode coating on a circular solid electrolyte wafer. The wafer is preferably made of stabilized zirconium oxide or other suitable material while the electrodes can be of platinum or other suitable materials deposited so as to form a surface which will be porous to oxygen ions. For ease of manufacture and assembly, the electrode coatings are preferably identical on each side of the wafer. The wafer is spaced from the inner wall of the tubular metal housing and forced against the flanged end of the housing by an outer cylindrical ceramic insulating sleeve which is telescoped inside the metal housing and a portion of the outer metal bushing. The outer insulating sleeve is forced against the outer end flange by an intermediate bushing which is externally threaded to engage internal threads in the outer bushing and internally threaded to engage an inner bushing. The outer insulating sleeve has a shouldered recess at its outer end which receives the outer annular edge portion of the flat inner surface of the wafer and surrounds the peripheral edge of the wafer. Positioned radially inwardly from the outer insulating sleeve is an inner insulating sleeve and an inner tubular metal member. The inner tubular metal member has a radially outwardly extending flange which contacts an annular portion of the inner electrode surface on the wafer. The flange on the inner tubular metal member is axially forced against the wafer by the inner insulating sleeve by means of the inner bushing member. The inner tubular metal member may have an insulated lead wire attached to it, or, where the intermediate bushing is made of non-conducting material such as machinable ceramic, the inner metal tubular member can extend out of the housing sufficiently far to permit direct attachment of external electrical circuit members.

The various parts of the sensor are easily assembled by placing the wafer in the recess in the outer ceramic insulating sleeve, inserting the wafer and outer ceramic sleeve into the housing and forcing it against the outer housing flange by means of the threaded intermediate bushing. The inner insulating sleeve and inner metal tube are then assembled together and forced against the wafer by the inner bushing. Preferably, high temperature ceramic fiber gaskets are placed at each end of the outer insulating sleeve in contact with the wafer and with the intermediate bushing to eliminate any opportunity for leakage of exhaust gases around the insulating sleeve. A pressure should be applied to the intermediate bushing member (about 5 inch pounds has been found satisfactory) to compress the gaskets slightly and provide an adequate seal. A similar gasket is also preferably used between the inner insulating sleeve and the inner bushing.

Since the oxygen sensor can experience temperature gradients of about 1200°F, the small differences in the coefficient of expansion of the outer stainless steel housing ($\alpha = 6.6 \times 10^{-6}$ per °F) and the insulating sleeves ($\alpha = 6.2 \times 10^{-6}$ per °F for Forstertite insulating ceramic) can be quite significant. For example, where the length of the outer tubular housing between the outer bushing and the point of contact with the wafer is 0.923 inches, an increase in length of about 0.0075 inches can be expected when the housing is heated to 1200°F. If the 1.220 inch long outer insulating sleeve and the 1.300 inch inner insulating sleeve were heated to 1200°F throughout their length, they would increase in length by 0.0097 inches and 0.010 inches, respectively, or more than the outer metal housing, thus increasing the sealing force as the exhaust becomes hottest and has its highest pressure. In actuality, the outer metal housing would have an average temperature increase somewhat less than 1200°F if its tip was 1200°F since the outer metal bushing portion which is attached to the exhaust pipe would be somewhat cooler. Likewise, the insulating sleeves would have a somewhat lower average temperature since a portion of their length lies adjacent the cooler outer bushing and the interior of the sensor is exposed to ambient air. Regardless of the exact amount of expansion that takes place in each element, tests have indicated that sensors assembled as described above have maintained a hermetic seal after repeated temperature cycling between ambient and 1200°F.

BRIEF DESCRIPTION OF THE DRAWINGS

FIG. 1 is a side sectional view of the principal embodiment of the improved oxygen sensor taken on line 1—1 of FIG. 4;

FIG. 2 is a side sectional view similar to FIG. 1 of a slightly modified embodiment;

FIG. 3 is a side sectional view of a one piece housing which may be substituted for the two piece housings in the embodiments of FIGS. 1 and 2; and FIG. 4 is a fragmentary end view of the oxygen sensor of FIG. 1.

DETAILED DESCRIPTION OF THE INVENTION

Referring to FIG. 1, the improved oxygen concentration measuring cell or oxygen sensor indicated generally at 10 comprises a metal housing 12 which includes an outer bushing member 14 having external threads 16, internal threads 18, and a hex head portion 20 which may be engaged by a suitable tool such as a spark plug socket wrench for mounting the unit in the side of an exhaust pipe (not shown). The bushing 14 is preferably formed of a metal such as series 430 stainless steel which is resistant to high temperature corrosion. A tubular portion 22, which is also preferably formed of stainless steel, is welded to the bushing 14 and 24. The inner end of the tubular portion 22 has a radially inwardly extending flange portion 28 which is slightly inset and spaced from the end of the housing. The inset flange eliminates the need for a sharp corner at the end of the housing that would tend to weaken it and also results in the solid electrolyte wafer 30 being slightly recessed in the housing and thus better protected from the possibility of being damaged by particles in the exhaust stream which may pass the end of the sensor.

The stabilized zirconium oxide wafer 30 is mounted in a recess defined by a sidewall portion 32 and a transverse shoulder portion 34 in the end of a ceramic tubular insulator member 36 which is axially forced against the wafer 30 and the end of the tubular housing 22 by an intermediate bushing member 40 which has external threads 42 in engagement with internal threads 18 in the outer bushing 14. The intermediate bushing 40 also has internal threads 44 for a purpose to be described later. The outer end surface of the intermediate bushing 40 includes aligned slot portions 46 which may be engaged by a wide bladed screwdriver or other tool to move the bushing 40 into or out of the interior of the sensor.

The wafer 30 has electrode coatings 50,52 such as platinum on each of its flat surfaces. Electrical contact is made to the electrode 50 on the exhaust gas side of the wafer 30 by housing flange portion 28. Electrical contact is made to the electrode 52 on the reference side of the wafer 30 by the radially outwardly extending flange 54 of a metal tube 56. Contact pressure is provided by the inner insulating sleeve 60 which is axially pressed against the flange 54 by inner threaded bushing 62. The inner bushing has external threads 64 which engage the internal threads 44 of the intermediate bushing. A knurled surface 66 on the end of bushing 62 permits pressure to be applied to insulating sleeve and contact flange 54.

It is extremely important that a hermetic seal be provided to prevent leakage of exhaust gases around the wafer since such leakage would result in an erratic voltage signal or no signal being produced between the electrodes 50,52. Although it should be theoretically possible to make the contact surfaces between the wafer 30, the flanges 28,54 and the insulating sleeve 36 so smooth that a gas tight seal would be effected, as a practical matter this is impossible. To insure a hermetic seal, we have provided high temperature ceramic fiber gaskets 70,72,74. The principal seal is provided by gasket 70. When the sensor 10 is assembled, a torque of about 5 inch pounds is applied to the intermediate bushing 40 to slightly compress the gasket 70. The gaskets preferably are able to withstand temperatures above 2000°F. Commonly available ceramic fiber gaskets contain a slight amount of organic binder which burns away during operation of the sensor but is sufficient to permit the gasket to be handled during assembly.

Since the three bushings 14,40 and 62 are each metal, it is obvious that inner metal tube 56 cannot be permitted to touch bushings 62 since an electrical short circuit to the outer housing and electrode 50 would be provided. Accordingly, tube 56 is recessed from bushing 62 and an insulated lead wire 78 is connected to the tube 56 and permitted to extend outside the sensor where electrical connections can be made to it. The outer electrode 50 is connected to the housing and exhaust pipe and thus to the electrical ground of the vehicle.

FIG. 2 is identical to FIG. 1 except that it substitutes a machinable ceramic intermediate bushing 40' for the metal bushing 40 of FIG. 1. Since the ceramic bushing 40' electrically insulates the inner bushing 62 from the outer bushing 14, it is possible to extend the inner metal tube 56' beyond the outer end of inner bushing 62 so that its outer end 82 can become an electrical connection point, thus eliminating the lead wire 78 and the operation required to attach it to tube 56.

FIG. 3 shows a modified one piece housing 12' which may be used in place of the welded two piece structure 12 of FIGS. 1 and 2. The housing 12' can be produced on an automatic screw machine from a stainless steel blank and for large scale production should be cheaper than the two piece welded construction of housing 12.

We claim as our invention:

1. A measuring cell for determining the concentration of oxygen in a mixture of exhaust gases comprising: a hollow metal housing member having mounting means adapted to be received in a complementary opening in a combustion engine exhaust system for positioning the inner end of said housing member within said exhaust system while leaving the outer end outside the exhaust system, said housing member having a radially inwardly extending annular flange portion at its inner end; a solid electrolyte wafer positioned inside said housing at the inner end thereof, said solid electrolyte wafer having a first electrode coating on a first side thereof in tight mechanical and electrical contact with said inwardly extending flange portion, said solid electrolyte wafer having a second electrode coating on its second side; a hollow tubular metal member positioned concentrically within said housing and having a radially outwardly extending annular flange portion of less maximum diameter than the wafer positioned in tight mechanical and electrical contact with said second electrode coating; a first tubular insulating sleeve positioned in surrounding relation to said hollow tubular metal member so as to exert axial pressure on said outwardly extending flange portion; a second tubular insulating sleeve positioned between said first tubular insulating sleeve and the inner wall of said housing, said second tubular insulating sleeve having a radial portion which spaces and insulates the edge of said electrolyte wafer from said metal housing, said second tubular insulating sleeve further having a transverse surface portion in axial engagement with the second side of said electrolyte wafer at a location radially outwardly of said radially outwardly extending flange portion of said tubular metal member, sealing means positioned at at least the axial juncture of said second tubular insulating sleeve and said electrolyte wafer; and threaded locking means for applying axial pressure to each of said insulating sleeves.

2. A measuring cell in accordance with claim 1 wherein said sealing means comprises high temperature gasket material formed of ceramic fibers.

3. A measuring cell in accordance with claim 2 wherein sealing means is further provided at the axial juncture of said threaded locking means and said first and second tubular insulating sleeves.

4. A measuring cell in accordance with claim 1 wherein said second insulating sleeve has a temperature coefficient of expansion less than that of the metal housing member and a length sufficiently greater than the length of the tubular portion of the housing between the mounting means and the first side of the electrolyte wafer to cause the second insulating sleeve to increase in length when said measuring cell is heated at least as much as said tubular portion of the housing.

5. A measuring cell in accordance with claim 4 wherein said tubular portion of the housing member is formed of stainless steel having a coefficient of expansion, in the temperature range from 32° – 1200°F, of about $6.6 \times 10^{-6}$/°F and said insulating sleeves are formed of ceramic having a coefficient of expansion in the same temperature range of about $6.2 \times 10^{-6}$/°F.

6. A measuring cell in accordance with claim 1 wherein said threaded locking means comprise a first annular locking member having external threads in engagement with internal threads in said metal housing member, and a second annular locking member having external threads in engagement with internal threads in said first annular locking member.

7. A measuring cell in accordance with claim 6 wherein one of said annular locking members is formed of an electrically insulating material.

8. A measuring cell in accordance with claim 6 wherein at least said first annular locking member includes tool engageable means at the external end thereof for facilitating rotation of said locking member in one direction by a complementary tool to apply axial pressure to said second tubular insulating sleeve or in the opposite direction to permit the removal of said locking member and all of the other elements within said metal housing.

9. A measuring cell in accordance with claim 1 wherein said hollow metal housing member comprises a hollow bushing portion having threads on portions of its internal and external surfaces and an elongated tubular portion welded to said bushing portion and forming the inner end portion of said housing member.

10. A measuring cell in accordance with claim 1 wherein said hollow metal housing is formed from a single piece of metal.

* * * * *